United States Patent [19]

Luk et al.

[11] 4,102,901

[45] Jul. 25, 1978

[54] ANTIBACTERIAL COMPOUNDS

[75] Inventors: Kong Luk, Cranleigh; John Peter Clayton, Horsham; Norman Harold Rogers, Rudgwick, all of England

[73] Assignee: Beecham Group Limited, Great Britain

[21] Appl. No.: 803,466

[22] Filed: Jun. 6, 1977

[30] Foreign Application Priority Data

Jun. 15, 1976 [GB] United Kingdom ............... 24712/76
Sep. 29, 1976 [GB] United Kingdom ............... 40472/76
Mar. 1, 1977 [GB] United Kingdom ................. 8647/77

[51] Int. Cl.$^2$ .................... C07D 309/06; A61K 31/35
[52] U.S. Cl. .......................... 260/345.8 R; 260/345.2; 260/343.44; 260/287 L; 260/287 R; 424/283; 424/279; 424/258; 260/345.7 R
[58] Field of Search ................. 260/345.7 R, 345.8 R

[56] References Cited

FOREIGN PATENT DOCUMENTS 1,395,907  5/1975  United Kingdom .......... 260/345.8 R

*Primary Examiner*—Nicky Chan
*Attorney, Agent, or Firm*—Jacobs & Jacobs

[57] ABSTRACT

Esters of an acid of formula:

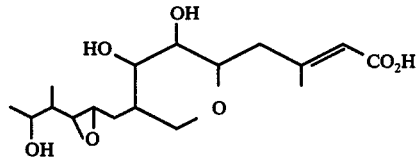

which is termed "monic acid" have activity against Gram-positive and Gram-negative organisms.

6 Claims, No Drawings

ANTIBACTERIAL COMPOUNDS

This invention relates to antibacterial compounds and in particular to a class of esters which have antibacterial activity against certain Gram-positive and Gram-negative organisms, in particular *Haemophilis influenzae* and *Neisseria gonorrhoae;* and also possess good antimycoplasmal activity. The compounds are therefore of value in the treatment of veterinary bacterial infections and of particular value in humans in the treatment of bronchitis and venereal disease.

The routine treatment for gonorrhoae has for many years been the use of penicillin antibiotics. However, some strains of gonococci are less sensitive to penicillins and the degree of such resistance has gradually increased resulting in larger doses of penicillins being required. Furthermore there have been reports of strains which produce penicillinase, and are thus highly resistant to penicillin therapy. The British Medical Journal (1976) at page 963 comments: "Now the outlook for the control of gonorrhoae has been radically changed for the worse by the portentous announcement of the existence of frankly resistant strains owing their resistance to the production of penicillinase, the penicillin-destroying enzyme found by many other bacterial species. This is wholly a new development, the consequences of which might well be disastrous."

This invention is concerned with a class of compounds which have high activities against many organisms including *N.gonorrhoae,* and as the compounds are completely unrelated to the β-lactam type of antibiotics (including penicillins and cephalosporins), they are completely unaffected by penicillinase.

Pseudomonic acid has the structure (I):

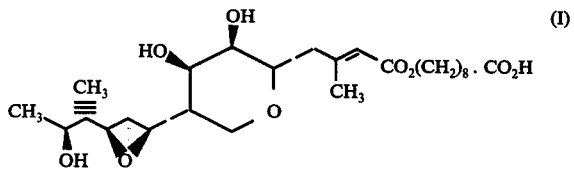

and is disclosed as having antibacterial activity in British Pat. No. 1,395,907. It has now been found that other esters of the allylic carboxylic acid moiety of the molecule also retain antibacterial activity.

Accordingly, the present invention provides a compound of formula (II):

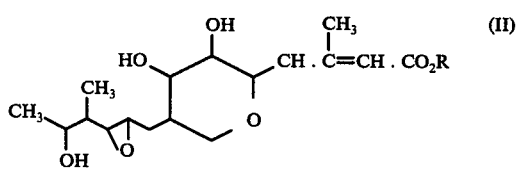

wherein R represents a pharmaceutically acceptable ester-forming radical, provided that R is not a group of formula $-(CH_2)_8CO_2H$ or an ester thereof.

The corresponding compound of formula (II) wherein R is hydrogen is described in our co-pending Application of even date. That compound in which the double bond is in the E configuration, we have designated "monic acid" and it will be referred to as such in this specification. The corresponding Z-isomer is termed "isomonic acid." It is believed that monic acid has the absolute stereochemistry as shown in formula (IIA):

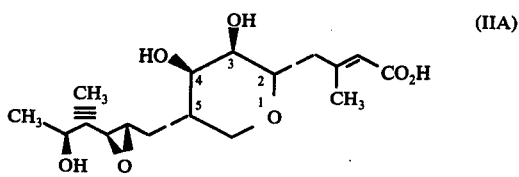

(The numbering is shown for the tetrahydropyran ring).

Suitable ester-forming radicals for the group R include:

(a) $C_{1-20}$alkyl, $C_{2-8}$ alkenyl or $C_{2-8}$ alkynyl each of which may be optionally substituted by $C_{3-7}$ cycloalkyl, halogen, carboxy, $C_{1-6}$alkoxycarbonyl, carbamoyl, aryl, heterocyclyl, hydroxy, $C_{1-6}$alkanoyloxy, amino, mono- and di- ($C_{1-6}$) alkylamino;

(b) $C_{3-7}$cycloalkyl optionally substituted with $C_{1-6}$alkyl;

(c) aryl;

(d) heterocyclyl.

The term "aryl" includes phenyl, and naphthyl optionally substituted with up to five halogen, $C_{1-6}$alkyl, $C_{1-6}$alkoxy, halo($C_{1-6}$)alkyl, hydroxy, amino, carboxy, $C_{1-6}$alkoxycarbonyl or $C_{1-6}$alkoxycarbonyl($C_{1-6}$)alkyl groups.

The term "heterocyclyl" includes single or fused rings comprising up to four hetero atoms in the ring selected from oxygen, nitrogen and sulphur and optionally substituted with up to three halogen, $C_{1-6}$alkyl, $C_{1-6}$alkoxy, halo($C_{1-6}$)alkyl, hydroxy, amino, carboxy, $C_{1-6}$alkoxycarbonyl, $C_{1-6}$alkoxycarbonyl($C_{1-6}$)alkyl, aryl or oxo groups.

One suitable substituted alkyl group for the group R has the formula (III):

wherein n is an integer from 1 to 7 or 9 to 20 and $R^1$ is hydrogen or a pharmaceutically acceptable salt-forming ion or $C_{1-6}$alkyl.

Another sub-class of esters of formula (II) comprises those compounds wherein the group R has the formula (IIIA):

wherein n is zero or 1 to 20, $R^2$ is $C_{1-6}$alkyl, and Q represents phenyl, $C_{1-6}$alkyl, $C_{3-7}$cycloalkyl, $C_{1-6}$alkoxycarbonylmethyl, benzyl, trifluoromethylbenzyl, halobenzyl.

Preferably, within formula (IIIA) n is zero or 1 to 3, $R^2$ is methyl and Q is phenyl, methyl, iso-propyl, n-hexyl, cyclohexyl, methoxycarbonylmethyl, benzyl, 3-trifluoromethylbenzyl.

Thus the group R in compound (II) may be for example $C_{1-6}$alkyl, in particular, methyl, ethyl n- or iso-propyl, n-, sec-, iso- or tert-butyl; halo-($C_{1-6}$)-alkyl such as trifluoromethyl, 2-chloroethyl, 2,2,2-trichloroethyl; aminoalkyl groups such as aminomethyl, 2-aminoethyl; hydroxymethyl, 2-hydroxyethyl; phenyl; substituted phenyl; a benzyl group; or a group of formula (III) wherein n is an integer from 1 to 7.

Other specific examples of the group R include: $C_{7-2\text{o}}$alkyl groups such as heptyl, octyl, nonyl, decyl and dodecyl; cyclopropyl, cyclopropylmethyl, cyclopentyl, cyclohexyl, methoxycarbonylmethyl, 2-methoxycarbonylethyl, 3-methoxycarbonylpropyl, 4-methoxycarbonyl-n-butyl, 5-methoxycarbonyl-n-pentyl, 6-methoxycarbonyl-hexyl, 7-methoxycarbonyl-n-heptyl, 10-methoxycarbonyldecyl, carbamoylmethyl, benzyl, 2,4,6-trichlorophenyl, pentachlorophenyl, o- or m; or p-methylphenyl, o-, m- or p-methoxycarbonylphenyl, 2- or 3- or 4-pyridyl, prop-2-enyl, prop-2-ynyl, 2-dialkylaminoethyl, or 3-methoxycarbonylprop-2-enyl.

Further specific groups R include the following:

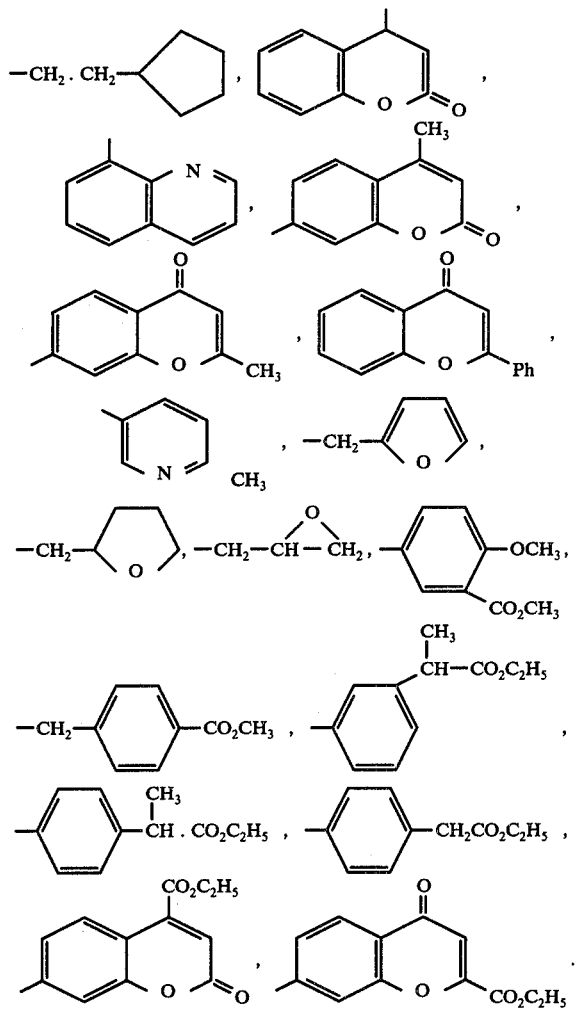

The compounds of this invention incorporate a trisubstituted double bond and may therefore exist in both the E (the natural) and Z (or iso) geometrical forms. It is to be understood that both geometrical isomers of any compound of formula (II) are included with the scope of this invention as well as mixtures of the two isomers. However, because in general the E-isomer of a particular structure has the greater activity, it is preferable to employ that isomer.

The compounds of the present invention may be prepared from the intermediate ketone of formula (IV) by any method known to convert a ketone into an $\alpha,\beta$-unsaturated ester. One such process comprises reacting a compound of formula (IV), in which the hydroxyl groups may be protected with a compound of formula (V) or (VI):

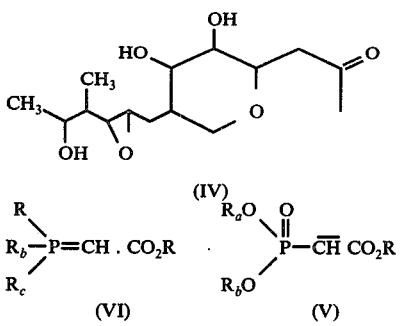

in which formulae (V) and (VI) the symbols $R_a$, $R_b$ and $R_c$ are the same or different and each is lower alkyl, aryl or aralkyl, and R is as defined with respect to formula (II) above; and subsequently removing any hydroxyl protecting groups.

The preferred embodiment of this process comprises reacting compound (IV) with compound (V). Preferably, in this case $R_a$ and $R_b$ are methyl or ethyl. In the case when compound (IV) is reacted with compound (VI), then $R_a$, $R_b$, and $R_c$ are preferably all phenyl.

The reaction is usually carried out in an inert solvent such as dimethylformamide, hexane, benzene, tetrahydrofuran for example, at a temperature of from about 10° to about 100° C preferably under an inert gas such as nitrogen. Under these conditions the reaction proceeds smoothly over a period of from a few minutes to a few hours and the product may be isolated by any of the usual techniques, e.g. solvent evaporation or anti-solvent precipitation followed by filtration. In many cases the reaction may be carried out in a solvent in which the product is insoluble and in such cases the precipitation solid may be collected by filtration. Purification of the product may be by any of the usual chromatographic or recrystallisation techniques.

Prior to the above process of this invention, it may be desirable to protect the hydroxyl groups in compound (IV). Although the reaction with the compound (V) or (VI) is possible without hydroxyl protection, in general higher yields of the product (II) are formed if the hydroxyl groups are protected. Again, such protecting groups must be removable under suitably mild conditions and suitable groups include silyl groups produced from a silylating agent as discussed above. Particularly suitable hydroxyl-protecting groups include trimethylsilyl, t-butyldimethylsilyl, methylthiomethyl. A preferred hydroxyl-protecting group is trimethylsilyl, as it is readily removed on completion of the reaction.

The compounds (II) may also be prepared by reacting the ketone of formula (IV) with:

(a) an ethynyl ether of formula (VII):

wherein R is as defined above with respect to formula (II) and subsequently treating the product with acid;

(b) an α-lithium carboxylic acid derivative of formula (VIII):

wherein R is as defined above with respect to formula (II), and $R^y$ is a silyl group, preferably trimethylsilyl;

(c) a malonic acid derivative of formula (IX):

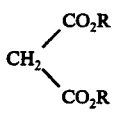  (IX)

wherein R is as defined above with respect to formula (II), in the presence of titanium chloride and pyridine;

(d) a reagent to convert compound (IV) to an enamine and subsequently reacting the enamine with a malonic acid derivative of formula (X):

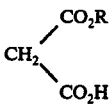  (X)

wherein R is as defined above with respect to formula (II). Compounds of formula (II) may also be prepared by esterification of monic acid or isomonic acid or a salt or other reactive derivative of the acid or transesterification of a compound of formula (II) wherein R is a different ester-forming radical. Esterification may be performed by any conventional method for example by reaction of the free acid:

(a) with the appropriate alcohol in the presence of a catalyst such as a strong acid, dry hydrogen chloride, or p-toluenesulphonic acid or
(b) with the appropriate halide or sulphate of the alcohol in the presence of dimethylsulphoxide and calcium carbonate or with the halide in the presence of hexamethylphosphoramide; or
(c) by phase transfer catalysis methods with the halide and/or sulphate of the alcohol in aqueous and/or organic solution in the presence of a quaternary ammonium salt such as tetrabutyl ammonium bisulphate or halide, or benzyltrimethyl-ammonium halide; or
(d) with a diazoalkane.

The formation of compounds (II) may also be carried out by conventional transesterification methods, for example reaction of an ester with the appropriate alcohol in the presence of a catalyst such as the sodium salt of the alcohol or dry hydrogen chloride, p-toluenesulphonic acid, or potassium cyanide. This process includes, of course, the transesterification of pseudomonic acid and esters thereof.

The compound of formula (IV) and its preparation is disclosed in our co-pending Application of even date.

The antibiotic compounds according to the invention may be formulated for administration in any convenient way for use in human or veterinary medicine, by analogy with other antibiotics, and the invention therefore includes within its scope a pharmaceutical composition comprising a compound of formula (II) above together with a pharmaceutical carrier or excipient.

The compositions may be formulated for administration by any route, and would depend on the disease being treated. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl-cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preserivatives, for example methyl or propyl p-hydroxybenzoate or sorbic acid, and if desired convention flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lypophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1 to 99% by weight, preferably from 10-60% by weight, of the active material, depending on the method of administration. Where the compositions comprise dosage units, each unit will preferably contain from 50-500 mg., of the active ingredient. The dosage as employed for adult human treatment will preferably range from 100 to 3000 mg., per day, for instance 1500 mg., per day, depending on the route and frequency of administration.

The following Examples illustrate this invention.

EXAMPLE 1

Preparation of Ethyl 4-[3R,4R-dihydroxy-5S-(2S,3S-epoxy-5S-hydroxy-4S-methylhexyl)-2,3,5,6-tetrahydropyran-2S-yl]-3-methylbut-2-enoate, E and Z isomers (ethyl monate and ethyl isomonate)

(a) Preparation of 2S-Acetonyl-3R,4R-dihydroxy-5S-(2S,3S-epoxy-5S-hydroxy-4S-methylhexyl)-2,3,5,6-tetrahydropyran (Compound A)

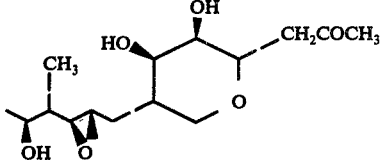

Ozonised oxygen (ca 1%) was bubbled through a solution of methyl pseudomonate (0.514 g) in methanol (8 ml) and pyridine (2 drops) at −78° C for 0.5 hour (when blue colour developed). The excess ozone was blown off by dry nitrogen at −78° C. Triethyl phosphite (80%. 0.3 ml) was then added and the reaction mixture was allowed to come to room temperature. The solvent was removed at room temperature in vacuo and the residue was chromatographed over silica gel (20 g). Elution of the column with chloroform-methanol (93:7) at the rate of 2 ml min$^{-1}$ gave the title compound (0.299 g), m.p. 85°–86° (from chloroform), $[\alpha]_D^{20}$ + 11.9° (c, 1.0, CHCl$_3$), $\nu$max. (CHCl$_3$) 1708, 1112, 1080, and 1050 cm$^{-1}$.

(b) Condensation of ketone A with triethyl phosphonoacetate with protection of hydroxy-groups Bistrimethylsilylacetamide (0.25 ml, 1 mmole) was added to a solution of 2-acetonyl-3,4-dihydroxy-5-(2,3-epoxy-5-hydroxy-4-methylhexyl)-2,3,5,6-tetrahydropyran (0.1 g, 0.33 mmole) in tetrahydrofuran (1 ml) at 0° C and then stirred at room temperature for 0.5 hour. The solvent was then completely removed in vacuo at room temperature and the residue dissolved in tetrahydrofuran (1 ml) for use in the next stage. Triethyl phosphonoacetate (0.075 g, 0.33 mmole) in tetrahydrofuran (2 ml) was added dropwise to a stirred suspension of sodium hydride (0.01 g, 80% dispersion in oil) in tetrahydroduran (2 ml) at 0° under nitrogen over 15 min. The reaction mixture was then stirred under nitrogen at room temperature for 1 hour. The solution of silylated 2-acetonyl-3,4-dihydroxy-5-(5-hydroxy-2,3-epoxy-4-methylhexyl)-2,3,5,6-tetrahydropyran was then added dropwise over 15 min. to the reaction mixture kept at 0°. This was then kept at 60° for 15 min. The reaction mixture was poured into ice-water (3 g) and acidified to pH 2, keeping the solution homogeneous by the addition of ethanol. After 2 min aqueous sodium bicarbonate (10 ml) was added and the mixture was saturated with sodium chloride and extracted continuously with ether. The ethereal extract was dried and evaporated to give a mixture showing some starting material and two major products on tlc. Preparative tlc (developed three times by chloroform-methanol (93:7) separated these products into two bands, A (Rf = 0.45) and B (Rf = 0.40). Extraction of Band A with ethyl acetate (100 ml) afforded ethyl 4-[3,4-dihydroxy-5-(2,3-epoxy-5-hydroxy-4-methylhexyl)-2,3,5,6-tetrahydropyran-2-yl]-3-methylbut-2Z-enoate (0.021 g), $\lambda$max 221 ($\epsilon$m 9,700)nm; $\nu$max (CHCl$_3$) 1690, 1640, 1262, 1155, 1085, and 1060 cm$^{-1}$; $\delta$ H (CDCl$_3$) 5.93 (1H, m, —C$\underline{H}$=), 4.25 (2H, q, J=7 Hz, —CO$_2$C$\underline{H}_2$CH$_3$), 2.06 (3H, s,

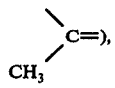

1.30 (3H, t, J=7 Hz, —CO$_2$CH$_2$C$\underline{H}_3$), 1.25 (3H, d, J=7 Hz, CH$_3$ C$\underline{H}$), and 0.96 (3H, d, J=7 Hz, C$\underline{H}_3$ CH); m/e (relative intensity) 372 (M+, 0.5), 354 (1), 336(2), 327(2), 309(4), 291(9), 227(100), 224(69), and 209(23) (Found: C, 61.85; H, 9.20%. C$_{19}$H$_{32}$O$_7$ requires C, 61.25; H, 8.5%). Extraction of Band B with ethyl acetate gave ethyl 4-[3,4-dihydroxy-5-(2,3-epoxy-5-hydroxy-4-methylhexyl)-2,3,5,6-tetrahydropyran-2-yl]-3-methylbut-2E-enoate (0.069 g), $[\alpha]_D$ − 1.44° (c, 1.8 CHCl$_3$); $\lambda$max 220 ($\epsilon$m 11,100) nm: $\epsilon$max (CHCl$_3$) 1705, 1650, 1155, and 1050 cm$^{-1}$; $\delta$H (CDCl$_3$) 5.86 (1H, m, —C$\underline{H}$=), 4.23 (2H, q, J=7 Hz, —CO$_2$CH$_2$CH$_3$), 2.70–2.90 (2H, m, $$-\text{CH}\underset{\diagdown}{\overset{\diagup}{\underline{\phantom{xx}}}}\overset{\text{O}}{\underset{\diagup}{\overset{\diagdown}{\underline{\phantom{xx}}}}}\text{CH}-),$$

2.26 (3H, s,

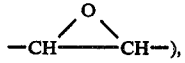

1.30 (3H, t, J=7 Hz, —CO$_2$CH$_2$C$\underline{H}_3$), 1.25 (3H, d, J=7 Hz, C$\underline{H}_3$CH), and 0.95 (3H, d, J=7 Hz, C$\underline{H}_3$CH); m/e (relative intensity) 372 (M+, 2), 354(2), 354(2), 336(3), 327(6), 309(7), 291(6), 270(11), 264(13), 245(10), 244(10), 227(100), 224(30), and 209(35) (Found: M+ 372.2150 C$_{19}$H$_{32}$O$_7$ requires M+ 372.2148).

EXAMPLE 2

Ethyl monate and Ethyl isomonate: Condensation of Ketone A with triethylphosphonoacetate without protection of the hydroxy-groups Triethyl phosphonoacetate (1.09 ml) in tetrahydrofuran (3 ml) was added dropwise to a stirred suspension of sodium hydride (0.086 g., 80% dispersion in oil) in tetrahydrofuran (2 ml) at 0° C under nitrogen over 15 min. The reaction mixture was then stirred under nitrogen at room temperature for 1 hour. A solution of 2-acetonyl-3,4-dihydroxy-5-(5-hydroxy-2,3-epoxy-4-methylhexyl)-2,3,5,6-tetrahydropyran (0.271 g) in tetrahydrofuran (2 ml) was added dropwise over 15 min., to the reaction mixture kept at 0° C. This was then kept at 60° C for 1.5 hour. The reaction mixture was poured into ice-water (20 ml) which was then saturated with sodium chloride. The organic layer was separated and the aqueous layer washed with ethyl acetate (2 × 30 ml). The combined organic extract was washed with brine (50ml), dried, and evaporated to give an oil which was filtered through a column of silica gel (30 g). Elution of the column with 2% methanol in chloroform (200 ml) followed by 4% methanol in chloroform (300 ml) at the rate of 1.5 ml min$^{-1}$ afforded 2 fractions. The first fraction was a complex mixture which was further purified by preparative tlc (developed 3 times with 8% methanol in chloroform) to give ethyl 4-[3,4-dihydroxy-5-(2,3-epoxy-5-hydroxy-4-methylhexyl)-2,3,5,6-tetrahydropyran-2-yl]-3-methylbut-2Z-enoate (0.017 g) (ethyl isomonate). The second fraction was ca 85% pure (h.p.l.c.) which was further purified by preparative tlc (developed 3 times with 8% methanol in chloroform) to give ethyl 4-[3,4-dihydroxy-5-(2,3-epoxy-5-hydroxy-4-methylhexyl)-2,3,5,6-tetrahydropyran-2-yl]-3-methylbut-2E-enoate (0.047 g). (ethyl monate)

EXAMPLE 3

Preparation of Methyl 4-[3R,4R-dihydroxy-5S-(2S,3S-epoxy-5S-hydroxy-4S-methylhexyl)-2,3,5,6-tetrahydropyran-2S-yl]-3-methylbut-2-enoate, E and Z isomers (methyl monate and methyl isomonate)

Bistrimethylsilylacetamide (5.9 ml) was added to a solution of 2- acetonyl-3,4-dihydroxy-5-(2,3-epoxy-5-hydroxy-4-methylhexyl)-2,3,5,6-tetrahydropyran (1.204 g) in acetonitrile (25 ml) at room temperature and the mixture was stirred at room temperature for 1 hour. The solvent was then completely evaporated in vacuo at 40° C and the residue was dissolved in N,N-dimethylformamide (3 ml) for use in the next stage. Trimethyl phosphonoacetate (3 g) in N,N-dimethylformamide (10 ml) was added dropwise over 0.5 h to a suspension of sodium hydride (80% dispersion in oil, 0.45 g) in N,N-dimethylformamide (10 ml) at 0° C under a nitrogen atmosphere. The reaction mixture was then stirred under nitrogen at room temperature for 1 hour. The solution of silylated ketone was then added dropwise over 0.5 hour, to the reaction mixture at 0° C under nitrogen which was then stirred at room temperature for 18 hours. The reaction mixture was poured into saturated brine (50 ml) and extracted with ethyl acetate (3 × 50 ml). The organic extract was dried and evaporated to give an oil which was dissolved in dioxane-water (4:1, 25 ml) and treated with hydrochloric acid (5M, 2 drops) for 10 min. Aqueous sodium bicarbonate (20 ml) was then added and the mixture extracted with ethyl acetate (3 × 30 ml). The organic extract was dried and evaporated to give an oil (1.2 g) which was chromatographed over silica gel (35 g). Elution of the column with chloroform-methanol (97:3) afforded 2 fractions. The first fraction was further purified by preparative tlc [developed with chloroform; methanol (92:8)] to give methyl isomonate (0.16 g) the Z-isomer as an oil. λmax (EtOH) 222 ($\epsilon_m$9,600) nm, νmax (CHCl$_3$) 1695, 1645, 1220 (broad), 1155, 1110, 1080, and 1050 cm$^{-1}$. The second fraction afforded methyl monate (0.4 g), the E-isomer m.p. 121°-122° from methyl acetate - hexane), $[\alpha]_D^{20}$ − 11.07° [C, 1.5 (CHCl$_3$)], λmax (EtOH) 221 ($\epsilon_m$14,700) nm, νmax (CHCl$_3$), 1710, 1645, 1435, 1220 (broad), 1155, 1110, and 1050 cm$^{-1}$.

EXAMPLE 4

Preparation of 4-[3R,4R-dihydroxy-5S-(2S,3S-epoxy-5S-hydroxy-4S-methylhexyl)-2,3,5,6-tetrahydropyran-2S-yl]-3-methylbut-2E-enoic acid (monic acid)

(a) From Pseudomonic Acid (without protection)

Sodium pseudomonate (10 mg) and potassium carbonate (15 mg) was dissolved in water (2 ml). The resulting solution was heated to 60° C and the reaction monitored by analytical high pressure liquid chromatography which after 1½ hours showed that optimum conversion to monic acid had occurred. To confirm the presence of monic acid, the reaction mixture was cooled, diluted with water (3 ml) saturated with sodium chloride, layered with ethyl acetate (10 ml) and the pH adjusted to 2.0 with rapid stirring. The organic layer was separated and the aqueous phase re-extracted with ethyl acetate (2 × 10 ml). The colourless ethyl acetate extracts were combined, treated with excess ethereal diazomethane and evaporated to dryness. The resulting mixture of esters were examined by h.p.l.c. in several solvent systems. The major peaks in the chromatogram were shown to have identical retention times with authentic samples of methyl monate and methyl pseudomonate, thereby confirming the presence of monic acid together with starting pseudomonic acid in the hydrolysate.

(b) From Methyl Monate

A solution of methyl monate (10 mg) in methanol (0.5 ml) was added to a solution of potassium carbonate (15 mg) in water (0.5 ml). The combined solution was heated to 60° C. After ½ hour, comparison of peak retention times with authentic monic acid by h.p.l.c. analysis confirmed the presence of monic acid in hydrolysate.

EXAMPLE 5

Preparation of monic acid from ketone A by Wittig condensation (i) Diethyl carboxymethylenephosphonate Triethyl phosphonoacetate (44.8 g, 0.2 M) was dissolved in 1N sodium hydroxide solution (200 ml; 0.2M) and stirred at room temperature overnight. The pH was adjusted from 9.0 to 1.0 with dilute hydrochloric acid. The solution was saturated with sodium chloride and extracted with ethyl acetate (3 × 100 ml). The latter was washed with saturated brine, dried over magnesium sulphate, filtered and evaporated to dryness in vacuo to give a viscous, colourless oil, which crystallized to a white solid when kept below room temperature (37.4 g; 96%). Thin layer chromatography revealed one component in chloroform at Rf = 0.02 as visualised with iodine vapour. $n_D^{23}$ = 1.3900.δ (CDCl$_3$) 9.33 (1H, s, CO$_2$H), 4.07 (4H, octet, Me—C$\underline{H}_2$—O—P, $J_{HH}$ = 6 Hz, $J_{HP}$ = 8 Hz), 2.88 (2H, d, P—C$\underline{H}_2$—CO$_2$H,$J_{HP}$ = 22 Hz) and 9.25 (6H, t, C$\underline{H}_3$—CH$_2$, J=6 Hz). Irradiation at δ 9.25 produces a doublet at 4.07 with $J_{HP}$ = 8 Hz, νmax(film) 1730 (C═O Str.), 1230 (P═O str.), 1170 (P—O vib.), 1050 (P—O vib.) cm$^{-1}$. (Found: C, 37.10; H, 7.07; P, 15.66%; C$_6$H$_{13}$PO$_5$ requires C, 36.74; H, 6.69; P, 15.79%).

(ii) Monic acid

N,O-Bistrimethylsilylacetamide (1.52 ml; 6mM) was added to a solution of 2-acetonyl-3,4-dihydroxy-5-(5-hydroxy-2,3-epoxy-4-methylhexyl)-2,3,5,6-tetrahydropyran (302 mg; 1mM) in dry acetonitrile (6 ml). The solution was stirred at room temperature for 1 hour followed by evaporation to dryness in vacuo at 40° C. The oily residue was dissolved in dry dimethylformamide (6 ml) for use in the next stage. Sodium hydride (114 mg; 80% pure; 3.8mM) was added portionwise over ½ hour to a solution of diethyl carboxymethylene phosphonate (392 mg; 2mM) in dry dimethylformamide (5 ml) at 0° under dry nitrogen. The mixture was stirred at 0° C for a further 2 hours. The solution of the silylated ketone above was added dropwise to this mixture at 0° C under nitrogen and the resulting reaction mixture stirred overnight at room temperature. The latter was evaporated to dryness and the dark residue dissolved in water (10 ml) and ethanol (10 ml) and the pH adjusted to 1.8. After 5 min., at room temperature the solution was diluted with water (15 ml) saturated with sodium chloride and extracted with ethyl acetate (4 × 10 ml). The latter was washed with brine, dried over magnesium sulphate, filtered and evaporated to dryness in vacuo to give monic acid. A sample of the resulting oil mixture was dissolved in ethyl acetate and treated with diazomethane, thus converting the monic acid present into methyl monate. The presence of the latter was confirmed by 4 analytical h.p.l.c. comparisons with authentic pure methyl monate.

EXAMPLE 6

Preparation of Benzyl 4-[3R, 4R-dihydroxy-5S-(2S, 3S-epoxy-5S-hydroxy-4S-methylhexyl)2,3,5,6-tetrahydropyran-2S-yl]-3-methyl-but-2E-enoate. (benzylmonate)

Bistrimethylsilylacetamide (3ml) was added to a solution of 2-acetonyl-3,4-dihydroxy-5-(2,3-epoxy-5-hydroxy-4-methylhexyl)-2,3,5,6-tetrahydropyran (0.604g, 2mM) in dry acetonitrile (10ml) and the mixture was stirred at room temperature for 1 hour. The solvent was then completely removed in vacuo at 40° C and the residue dissolved in dimethylformamide (5ml) for the next stage.

Diethyl benzyloxycarbonylmethylenephosphonate (2.30g; (8mM) in dry dimethylformamide (5ml) was added dropwise to a suspension of sodium hydride (80% dispersion in oil, 0.240g; 8mM) in dry dimethylformamide (5ml) at 0° C under nitrogen. The solution was stirred under nitrogen at room temperature for 1 hour. The solution of silylated ketone was then added dropwise over 0.5 hour, to the reaction mixture at 0° C under nitrogen, which was then stirred at room temperature for 18 hours. The solution was evaporated to dryness and the residual yellow oil dissolved in ethyl acetate, washed with brine and evaporated to an oil. The latter was dissolved in dioxan/water (4:1; 10ml) and concentrated hydrochloric acid added to pH 1.5 followed by stirring at room temperature for 10 minutes. Excess sodium bicarbonate solution was added and the mixture was then extracted with ethyl acetate which was washed with brine, dried over magnesium sulphate, filtered and evaporated to an oil (1.615g). This oil was chromatographed on silica (40g) eluting with gradient of methanol/chloroform 1 to 3%. The fractions containing pure benzyl monate (by hplc and tlc) were collected and evaporated to an oil (0.150g), $[\alpha]_D^{20}$ −5.0° (c,1.0 CHCl$_3$). λmax (EtOH) 219 (εm 14,000)nm; νmax (CHCl$_3$), 3,400 (broad, OH's), 1710 (broad, C=O's), 1645cm$^{-1}$; δH (CDCl$_3$) 7.26 (5H, s, Ph), 5.75 (1H, s, CH=C), 5.08 (2H, s, PhC$\underline{H}_2$), 2.70 (2H, m,

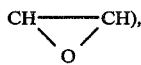

2.18 (3H, s,

1.17 (3H, d, J = 7Hz, CH-C$\underline{H}_3$) and 0.88 (3H, d, J = 7Hz, CH—CH$_3$); m/e 506 (M+), 488, 444, 91. (Found: M = 434.229970 C$_{24}$H$_{34}$O$_7$ requires 434.230435).

EXAMPLE 7

4-[3R,4R-Dihydroxy-5S-(2S,3S-epoxy-5S-hydroxy-4S-methylhexyl)-2,3,5,6-tetrahydropyran-2S-yl]-3-methyl-but-2E-enoic acid (Monic Acid) (with protection)

Pseudomonic acid (10g; 20mM) was dissolved in trimethyl orthoformate (50ml). p-Toluenesulphonic acid (20mg) was added and the solution was stirred at room temperature for ½ hour, followed by evaporation to dryness in vacuo. The resulting oil was dissolved in 1N sodium hydroxide solution (100ml; 100mM) and the solution stirred at 65° C for 2 hours. After completion of the hydrolysis (hplc) the solution was cooled and the pH adjusted to 7.0 with hydrochloric acid. Methanol (75ml) was added, the pH was adjusted to 2.0 with 5N hydrochloric acid and the reaction mixture stirred at room temperature for 0.25 hour. The pH was readjusted to 9-9.5 with sodium hydroxide solution and maintained until complete hydrolysis of the O-formate (c.a. 3 hours at room temperature; hplc). The pH was adjusted to 7.0 and the solution evaporated to small bulk (10 - 20ml), saturated with sodium chloride, layered with ethyl acetate and with stirring the pH was adjusted to 3.0. The ethyl acetate layer was separated, washed with saturated brine, dried over magnesium sulphate and evaporated to an oil, which was dissolved in water by addition of 1N sodium hydroxide solution to pH 7.5. The resulting solution of sodium monate and sodium 9-hydroxynonanoate was evaporated to dryness in vacuo (12.64g). This solid was extracted with ethanol (2 × 50ml) and filtered. The ethanol filtrate was evaporated to dryness to give sodium monate (9.62g) as a white solid. The latter was dissolved in water with ethyl acetate and acidified to pH 3.0. The ethyl acetate extract was washed with saturated brine, dried over magnesium sulphate and evaporated in vacuo to an oil (8.48g). Trituration with dry ether afforded monic acid as a white solid, which was collected and dried (2.62g; 38%), m.p. 133°-135° C (crystals from ethanol m.p. 146°-147° C) (Found: C, 59.0; 8.2% C$_{17}$H$_{28}$O$_7$ requires C, 59.3; H, 8.2%). Tlc revealed a single component Rf = 0.44 in chloroform, acetone, acetic acid 12:5:3 and a single peak by hplc $[\alpha]_D$ − 13°(c, 1.0EtOH) and −20° (c, 1.0 1% NaHCO$_3$), νmax (KBr) 3300, 2960, 2950, 1690, 1640, 1450, 1250cm$^{-1}$, λmax 221nm (εm 11,200), δ$_H$(db-DMSO) 5.55 (1H,s,=C$\underline{H}$), 2.05 (3H,s,

1.05 (3H,d,>CHCH$_3$) and 0.80 (3H,d,>CHC$\underline{H}_3$) δ$_C$ (d$^6$-DMSO) (2 signals under the DMSO peaks) 167.3, 156.4, 117.6, 74.5, 69.4, 68.2, 67.7, 64.6, 59.0, 54.6, 37.3, 31,47, 20.0, 18.4 and 11.6, m/e 227 (82%, M+ − H$_2$O − C$_5$H$_7$O$_2$), 141 (43%) 111 (100%).

EXAMPLE 8

Sodium Monate

Monic Acid prepared in Example 7 (3.44g; 1mM) was suspended in water (10ml). N/10 sodium hydroxide solution (10ml; 1mM) was added to the stirred suspension until complete solution was obtained (pH 7.5). The latter was freeze dried and finally dried in vacuo over P$_2$O$_5$. (3.66g; 100%). $[\alpha]_D$ − 20° (c,1.0 H$_2$O) νmax (KBr) 3400, 2970, 1650, 1550cm$^{-1}$., λmax (EtOH) 214nm (εm 14,600), δ$_H$ (d$^6$-DMSO) 5.16 (1H,s, =C$\underline{H}$), 1.95 (3H,s, =CCH₃), 1.05 (3H,d,>CHCH₃) and 0.79 (3H,d,>CHCH₃).

EXAMPLE 9

Methyl 4-[3R, 4R-Dihydroxy-5S-(2S,3S-epoxy-5S-hydroxy-4S-methylhexyl)-2,3,5,6-tetrahydropyran-2S-yl]-3-methylbut-2E-enoate (methyl monate).

Sodium monate prepared in Example 8 (1.12g) was dissolved in dry methylformamide and 5 drops of hexamethylphosphoramide. Methyl iodide (5ml) was added and the reaction mixture was stirred overnight at room temperature. Evaporation to dryness in vacuo afforded a residue, which was partitioned between ethyl acetate and water and the ethyl layer was separated washed with sodium bicarbonate solution, brine, dried over magnesium sulphate and evaporated to an oil (0.63g). The latter was dissolved in ether from which methyl monate crystallised (0.45g; 50%) m.p. 124°–125° (no depression of mixed m.p. was observed with authentic material from example 3).

EXAMPLE 10

Preparation of Ethyl Monate

The sodium monate (0.80g) was dissolved in N,N-dimethylformamide (7.5ml) and hexamethylphosphoramide (7 drops) then treated with ethyl iodide (1ml) and stirred at room temperature for 24 hours. After evaporation to dryness, the oil was dissolved in ethyl acetate and washed with sodium bicarbonate and brine. The solution was dried (MgSO₄) and evaporated to an oil which crystallised on standing. Then the product was filtered and washed with ether (0.55g, 68%) m.p. 96°–7° C, spectroscopically and chromatographically identical with material described in example 2.

EXAMPLE 11

Preparation of Methoxycarbonylmethyl 4-[3R,4R-dihydroxy-5S-(2S,3S-epoxy-5S-hydroxy-4S-methylhexyl)-2,3,5,6-tetrahydropyran2S-yl]-3-methylbut-2E-enoate. (Methoxycarbonylmethyl monate)

Sodium 4-[3R,4R-dihydroxy-5S(2S,3S-epoxy-5S-hydroxy-4S-methylhexyl)-2,3,5,6-tetrahydropyran-2S-yl]-3-methylbut-2E-enoate (1.098gm; 3.0mM) was dissolved in dry dimethylformamide (15ml) and hexamethylphosphoramide (15 drops). Methyl bromoacetate (0.918gm; 6.0mM) was added and the reaction mixture stirred at room temperature for 18 hours. The solvent was then removed at reduced pressure and the residue partitioned between ethyl acetate and saturated sodium bicarbonate solution. The organic layer was washed with brine and dried over anhydrous magnesium sulphate. Removal at reduced pressure gave a yellow oil (1.983gm). This oil was purified by column chromatography over silica gel (Type 60; 80gm). Elution with 5% methanol/chloroform afforded the pure methoxycarbonylmethyl monate (by tlc and hplc) as a colourless oil, which on trituration with dry diethyl ether gave a white solid (0.580gm; 46.5%). M.pt. 89°–91° C (Found: C, 57.45; H, 7.85. C₂₀H₃₂O₉ requires: C, 57.68; H, 7.74%). [α]$_D^{20}$ = −8.22° (c,1% CHCl₃) λmax (EtOH) 225nm (13,600). νmax (CHBr₃) 3450, 1745, 1723 and 1645cm⁻¹. δ$_H$ (CDCl₃) 5.80 (1H,s, —CH=C); 4.57 (2H,s, CO₂CH₂CO₂); 3.70 (s,CO₂CH₃); 2.18 (3H,s,

1.19 (3H,d,J = 6.7Hz, CH₃−14); 0.90 (3H,d,J = 6.7Hz, CH₃−17), δ$_C$ (CDCl₃) 169.0, 165.6, 159.7, 116.2, 74.8, 71.3, 70.4, 68.8, 65.4, 61.3, 60.0, 55.5, 52.2, 42.8, 39.5, 31.6, 20.8, 19.4, 12.6. m/e 227.1318(35%), 125(12%; 227 —C₅H₁₀O₂), 111(70%) 69(100%), no M⁺.

EXAMPLE 12

Preparation of 4-Methoxycarbonylbutyl-4-[3R,4R-dihydroxy5S-(2S,3S-epoxy-5S-hydroxy-4S-methylhexyl)-2,3,5,6-tetrahydropyran-2S-yl]-3-methylbut-2E-enoate (4-Methoxycarbonylbutyl monate)

The sodium salt of 4-[3R,4R-dihydroxy-5S-(2S,3S-epoxy-5S-hydroxy-4S-methylhexyl)-2,3,5,6-tetrahydropyran-2S-yl]-3-methylbut-2E-enoic acid (0.50gm; 1.366mM) was dissolved in dry dimethylformamide (15ml) and stirred at room temperature for eighteen hours with methyl 5-bromovalerate (0.533gm; 2.732mM) and hexamethylphosphoramide (15 drops). The solvent was then removed at reduced pressure and the residue partitioned between ethyl acetate and saturated sodium chloride solution and dried over anhydrous magnesium sulphate. Filtration and removal of the solvent at reduced pressure gave a pale yellow oil, which partially solidified on standing (0.810gm). The product was purified by column chromatography over silica gel (Type 60; 30gm). Elution with 5% methanol/chloroform gave the pure 4-methoxycarbonylbutyl monate (by tlc and hplc) as a colourless oil, which on trituration with diethyl ether yielded a white solid (0.377gm; 60%) M.pt. 75°–76° C (ethyl actetate/petroleum ether 40–60). (Found: C, 60.16; H, 8.31; C₂₃H₃₈O₉ requires: C, 60.25; H, 8.35%). [α]$_D^{20}$ − 8.88° (c, 1% CHCl₃). νmax (KBr) 3460, 1735, 1710 and 1640cm⁻¹. δ$_H$ (CDCl₃) 5.72 (1H,s,CH=C); 3.64 (3H,s,CO₂CH₃); 2.18 (3H,s,

1.20 (3H,d,J = 7.6Hz,>CHCH₃); 0.92 (3H,d,J = 7.6Hz,>CHCH₃); δ$_C$(CDCl₃) 173.9, 166.7, 157.3, 117.3, 74.8, 71.0, 70.3, 68.9, 65.4, 63.2, 61.1, 55.6, 51.5, 42.8, 39.6, 33.5, 31.6, 28.1, 21.5, 20.7, 19.1, 12.6, m/e440 (0.8%; M⁺-H₂O), 356 (0.9%; —C₅H₁₀O₂), 327 (0.8%; —O(CH₂)₄CO₂CH₃), 309 (2%; 327 - H₂O), 227 (35%), 214 (5%), 209 (5%), 125 (10%), 115 (100%), 111 (43%).

EXAMPLE 13

Preparation of 10-Methoxycarbonyldecyl 4-[3R,4R-dihydroxy5S-(2S,3S-epoxy-5S-hydroxy-4S-methylhexyl)-2,3,5,6-tetrahydropyran-2S-yl]-3-methylbut-2E-enoate (10-Methoxycarbonyldecyl monate)

The sodium salt of 4-[3R,4R-dihydroxy-5S-(2S,3S-epoxy-5S-hydroxy-4S-methylhexyl)-2,3,5,6-tetrahydropyran-2S-yl]-3-methylbut2E-enoic acid (0.750gm; 2.05mM) was dissolved in dry dimethylformamide (25ml) and stirred at room temperature for 18 hours with methyl 11-bromoundecanoate (1.145gm; 4.10mM) and hexamethylphosphoramide (25 drops). The solvent was then removed at reduced pressure and the residue partitioned between ethyl acetate and saturated sodium bicarbonate solution. The organic layer was washed with saturated sodium solution and dried over anhydrous magnesium sulphate. Filtration and removal of solvent at reduced pressure gave a pale yellow oil, which partially crystallised on standing (1.84gm). Column chromatography over silica gel (Type 60; 75gm), eluting with 5% methanol/chloroform gave the pure 10-methoxycarbonyldecyl monat (hplc and tlc) as a colourless oil. Trituration with dry ether gave a white solid (0.619gm; 56%). m.pt. 75°–76° C (ethyl acetate/hexane). (Found: C, 64.23; H, 9.47. $C_{29}H_{50}O_9$ requires: C, 64.18; H, 9.29%). $[\alpha]_D^{20}$ − 748° (c, 1% $CHCl_3$). $\lambda$max (EtOH) 222nm ($\epsilon$m 13,400). $\nu$max ($CHBr_3$) 3450, 1739, 1710 and 1645cm$^{-1}$. $\delta_H$ ($CDCl_3$) 5.70 (1H,s,C$\underline{H}$=C); 3.61 (3H,s,CO$_2$C$\underline{H}_3$); 2.18 (3H,s, C$\underline{H}_3$ - C=C; 0.91 (3H,d,J = 6.Hz CHC$\underline{H}_3$). $\delta_C$($CDCl_3$) 174.4, 166.8, 156.6, 117.7, 74.9, 70.4, 69.1, 65.9, 61.3, 55.6, 51.4, 42.8, 39.5, 117.7, 34.1, 31.7, 29.2, 28.7, 26.0, 25.0, 20.8, 19.1, 12.7, m/e 524 (1.5%; M$^+$ - H$_2$O), 440 (1%; - C$_5$H$_{10}$O$_2$), 327 (>5%, M$^+$ —O(CH$_2$)$_{10}$ CO$_2$C$\underline{H}_3$), 309 (2%, 327 - H$_2$O), 298 (22%; [H$_2$C:C(C$\underline{H}_3$).CH$_2$CO$_2$(CH$_2$)$_{10}$CO$_2$C$\underline{H}_3$]$^+$), 227 (100%), 209 (15%; 227 - H$_2$O), no M$^+$.

EXAMPLE 14

Phenyl Monate

Isobutyl chloroformate (136mgs) was added to an almost clear solution of monic acid (344mgs) in methylene chloride (10ml) tetrahydrofuran (1ml) and triethylamine (10mgs) with pyridine (1 drop) at −10° to 15° C. After stirring at ca −10° C for ½ hour, phenol (188mgs) was added and reaction allowed to reach ambient temperature. The solution was evaporated to dryness and residue dissolved in ethyl acetate/water. Separation of organic layer washing with water (pH 10.5, twice) then brine and evaporation after drying (MgSO$_4$) yielded an oil. The oil was chromatographed on silica gel (20g) eluting with gradient of methanol/chloroform 2 to 5%. Fractions containing pure phenyl monate (by tlc and hplc) were collected and evaporated to an oil (260mgs, 62%), $[\alpha]_D^{20}$ − 15.1° (c, 1.0 CHCl$_3$), $\lambda$max (EtOH) 227 ($\epsilon$m 14,100)nm, $\nu$max (CHCl$_3$) 3,400 (broad, OH's), 1730 (broad, C=O's), 1645 and 910cm$^{-1}$, $\delta_H$ (CDCl$_3$) 6.9 − 7.5 (5H,m, Ph), 5192 (1H,s,C$\underline{H}$=C), 2.67 (2H,m,

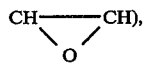

2.18 (3H,s,

0.88 (3H,d,J = 8Hz, CH-C$\underline{H}_3$), $\delta_C$(CDCl$_3$) 164.9, 160.4, 150.6, 129.3, (two signals), 125.6, 121.7 (two signals), 116.5, 74.8, 71.2, 70.2, 68.9, 65.4, 61.3, 55.6, 43.1, 42.8, 39.6, 31.6, 20.8, 19.4, 12.7.

EXAMPLE 15 p-Methoxycarbonylphenyl monate

Isobutyl chloroformate (136mgs) was added to a solution of monic acid (244mgs) and triethylamine (101mgs) in THF (15ml) at −10° to −15° C. After stirring for ½ hour at ca −10° C a solution of methyl p-hydroxybenzoate (340mgs) in THF (1ml) was added and the reaction stirred for 1 hour at 0° C then 1 hour at room temperature. Filtration and evaporation yielded an oil which was dissolved in ethyl acetate, washed with sodium bicarbonate and brine then dried (MgSO$_4$). Evaporation yielded an oil which was chromatographed on silica (20g) eluting with gradient of methanol/chloroform 0–5%. Fractions containing pure product (by tlc, hplc) were collected and evaporated to an oil (325mgs, 68%), $[\alpha]_D^{20}$ = 19.1° (C,1.0 CHCl$_3$), $\lambda$max (EtOH) 241 ($\epsilon$ 20, 763)nm, $\nu$max (CHCl$_3$) 3,400 (broad), 1720 (broad), 1282 and 1110cm$^{-1}$, $\delta_H$ (CDCl$_3$) 7.97 (2H,d,J=9Hz,

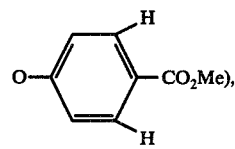

7.11 (2H,d,J=9Hz,

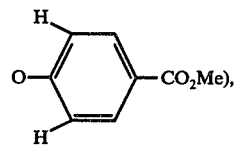

5.92 (1H,s,C$\underline{H}$=C), 3.85 (3H,s,OC$\underline{H}_3$), 2.23 (3H,s,

1.18 (3H,d,J=6Hz, CHC$\underline{H}_3$), 0.88 (3H,d,J=6Hz,CHC$\underline{H}_3$), $\delta_C$(CDCl$_3$) 166.6, 164.2, 161.6, 154.5, 131.1 (two signals), 127.3, 121.8 (two signals), 116.2, 74.8, 71.2, 70.3, 68.9, 65.5, 61.2, 55.7, 52.2, 43.2, 42.8, 39.7, 31.6, 20.7, 19.5, and 12.7.

EXAMPLE 16

3-Pyridyl monate

A solution of monic acid (172mgs) in THF (10ml) and triethylamine (69$\mu$l) at −10° to −15° C was treated with isobutyl chloroformate (65$\mu$l) and pyridine (1 drop). The reaction was stirred for ½ hour at ca. −10° C then a solution of 3-hydroxypyridine (95mgs) in THF (1ml) and triethylamine (140ml) was added. After stirring at 0° C for 1 hour and 1 hour at room temperature the reaction mixture was evaporated to an oil, dissolved in ethyl acetate/ water and the organic layer washed with sodium bicarbonate then brine. Evaporation to dryness yielded an oil which was chromatographed on silica (10g) eluting with a gradient of methanol/chloroform 0 to 5%. Fractions containing pure product (by tlc, hplc) were collected and evaporated to an oil (83mgs; 39%), $[\alpha]_D^{20}$ = −18.8° (C,1.0 CHCl$_3$) $\lambda$max (EtOH) 231 ($\epsilon$ 13,000)nm, (1H,m,pyridyl 6-H) 3400(broad), 1642 and 1120cm$^{-1}$; $\delta$ (CDCl$_3$) 8.35 (1H,s,pyridyl 2-H), 5.94 (1H,s,CH=C), 2.23 (3H,s,

1.18 (3H,d,CHC$\underline{H}_3$), 0.90 (3H,d,CHC$\underline{H}_3$) 164.1, 162.2, 147.6, 146.3, 143.5, 129.7, 124.0, 115.8, 74.8, 71.3, 70.4, 71.3, 70.4, 68.9, 65.5, 61.3, 55.6, 43.3, 42.9, 39.8, 31.6, 20.8, 19.6, and 12.7.

EXAMPLE 17

4-Coumaryl monate

Isobutyl chloroformate (65ml) was added to a solution of monic acid (172mgs) and triethylamine (69μl) in THF (8ml) at −10° C followed by pyridine (1 drop). After half an hour at −5° to −10° C, a solution of 4-hydroxycoumarin (162mgs) in THF (2ml) and triethylamine (140μl) was added and reaction stirred at 0° C for 1 hour then room temperature for 1 hour. The reaction mixture was evaporated to dryness. The residue was partitioned between ethyl acetate and water and the organic layer washed with sodium bicarbonate and brine. After drying (MgSO$_4$) the solution was evaporated to an oil and chromatographed on silica (10g) eluting with gradient of methanol/chloroform 2-5%. Fractions containing pure product (by tlc) were collected and evaporated to an oil (130mgs, 53%), $[\alpha]_D^{20}$ = 13.0° (c,1.0 CHCl$_3$) νmax 3400 (broad, OH's), 1755, 1720 (C=O'S) and 1620cm$^{-1}$, $\delta_H$(CDCl$_3$) 7-7.7 (4H,m, C$_6$H$_4$) 6.45 (1H,s, COC$\underline{H}$=). 6.00 (1H,s,CH=C), 2.27 (3$\underline{H}$,s,C$\underline{H}_3$-C=C), 1.18 (3H,d,C$\underline{H}_3$—CH), 0.90 (3H,d,C$\underline{H}_3$—CH), $\delta_C$ (CDCl$_3$) 165.4, 162.2, 161.6, 159, 153.6, 132.7, 124.4, 123.1, 116.9, 116.2, 115.8, 114.9, 104,4, 74.8, 71.4, 70.3, 68.8, 65.6, 61.3, 55.6, 43.5, 42.8, 39.8, 31.6, 20.8, 19.9, 20.7.

EXAMPLE 18

α R,S,-Methoxycarbonylbenzyl monate

Methyl α-bromophenylacetate (390mgs; 1.70mM) was added to a solution of sodium monate (311mgs; 0.85mM) in dry dimethylformamide (10ml) containing hexamethylphosphoramide (10drops) and the solution was stirred at room temperature for 23 hours. The reaction mixture was evaporated to dryness and the resulting oil was dissolved in ethyl acetate. The latter was washed with sodium bicarbonate, brine, dried over magnesium sulphate. Filtration and removal of the solvent in vacuo afforded an oil (710mg), which was chromatographed over silica gel (Type 60; 28g) eluting with a gradient from chloroform to 8% methanol/chloroform to give α R,S-Methoxycarbonylbenzyl monate 310mgs) (72%) as a white foam (pure by tlc and hplc). $[\alpha]_D^{20}$= 1.8 (c,1.0 CHCl$_3$). λmax (EtOH) 223nm (εm 18,300), νmax (CHCl$_3$) 3400, 2950, 1750, 1720, 1640, 1500, 1450, 1430cm$^{-1}$, δH (CDCl$_3$) 7.3 (5H,m,

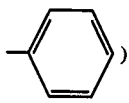

5.88 (1H,s,αCH), 5.84, (1H,s,C$\underline{H}$=C), 3.65 (3H,s,CO$_2$C$\underline{H}_3$), 2.18, (3H,s,

1.18 (3H,d, C$\underline{H}_3$ -14) and 0.88 (3H,d,C$\underline{H}_3$ -17), $\delta_c$ (CDCl$_3$) 169.9, 165.6, 159.8, 129.1, 128.8, 127.7, 116.4, 74.9, 73.9, 71.4, 70.3, 68.9, and 68.7, 65.4, 61.3, 55.5, and 55.3, 52.6, 42.8, 42.7, 39.5, 31.6, 20.8, 19.6, 19.3, and 12.7, m/e 492 (M+), 227 (3%), 100%). (Found: M=492.2436, C$_{26}$H$_{36}$O$_9$ requires 492.2360).

EXAMPLE 19

1 R,S - Methoxycarbonylethyl monate

Methyl 2-bromopropionate (167mg; 1mM) was added to a solution of sodium monate (183mg, 0.5mM) in dry dimethylformamide (5ml) containing hexamethylphosphoramide (5 drops) and the solution was stirred at room temperature for 17 hours. The reaction mixture was evaporated to dryness and the resulting oil was dissolved in ethyl acetate. The latter was washed with sodium bicarbonate solution, brine, dried over magnesium sulphate. Filtration and removal of the solvent in vacuo afforded an oil (181mg) which was chromatographed over silica gel (Type 60, 12g) eluting with a gradient from chloroform to 6% methanol/chloroform to give 1 R,S, - methoxycarbonylethyl monate (150mg; 70%) as an oil (pure by tlc and hplc.). $[\alpha]_D^{20}$− 11.6° (c,1.0 CHCl$_3$). λmax (EtOH) 224nm (εm13,600), νmax (CHCl$_3$) 3400, 2950, 1750, 1720, 1640, 1450, 1415cm$^{-1}$, $\delta_H$(CDCl$_3$) 5.78 (1H,s,C$\underline{H}$=C), 5.05 (1H,q,α-C$\underline{H}$), 3.68 (3H,s, CO$_2$C$\underline{H}_3$) 2.16 (3H,s,

C=C),

CH$_3$ 1.56 (3H,d,β-C$\underline{H}_3$), 1.19 (3H,d, C$\underline{H}_3$-14) and 0.90 (3H,d,CH$_3$-17), $\delta_c$ (CDCl$_3$), 171.9, 165.7 (split), 159.0, 116.7, 75.0, 71.3, 70.5 and 70.3, 69.0, and 68.9, 68.0, 65.5, 61.3, 55.5 (split), 52.2, 43.1, and 42.8, 39.6, and 39.4, 31.7, and 31.5, 21.0 and 20.9, 19.5, and 19.3, 17.1 and 16.9 and 12.6, m/e 430 (M$^+$<1%) 227 (42%), 111 (100%). (Found: M=430.2179, C$_{21}$H$_{34}$O$_9$ requires 430.2203).

EXAMPLE 20

Preparation of 5-Methoxycarbonylpentyl 4-[3R,4R-dihydroxy-5S-(2S,3S-epoxy-5S-hydroxy-4S-methylhexyl)-2,3,5,6-tetrahydropyran-2S-yl]-3-methyl-but-3E-enoate. (5-methoxycarbonylpentyl monate.)

The sodium salt of 4-[3R,4R-dihydroxy-5S-(2S,3S-epoxy-5S-hydroxy-4S-methylhexyl)-2,3,5,6-tetrahydropyran-2S-yl]-3-methylbut-2E-enoic acid (0.8gm; 2.19mM) was dissolved in dry dimethylformamide (15ml) and stirred at room temperature for 18 hours with methyl 6-bromohexanoate (1.7gm; 8.13mM) and hexamethylphosphoramide 15 drops). The solvent was then removed at reduced pressure and the residue partitioned between ethyl acetate and saturated sodium bicarbonate solution. The organic layer was washed with saturated sodium chloride solution and dried over anhydrous magnesium sulphate. Filtration and removal of the solvent at reduced pressure gave a pale yellow oil (1.72gm) which was purified by column chromatography over silica gel (35gm; Type 60). Elution with 5% methanol/chloroform gave the pure 5-methoxycarbonylpentyl monate (by tlc and hplc) as a colourless oil, which on trituration with diethyl ether yielded a white solid (0.250gm; 24%). M.pt. 59°-61° C. (found: C,60.87; H, 8.37. C$_{24}$H$_{40}$O$_9$ requires: C, 61.00; H, 8.53%). $[\alpha]_D^{20}$− 8.94 (C, 1% CHCl$_3$), λmax (EtOH) 222nm (εm 14,200) νmax (KBr) 3480, 1740, 1710, 1645cm$^{-1}$. $\delta_H$ (CDCl$_3$) 5.69 (1H,s,C$\underline{H}$=C), 3.61 (3H,s,CO$_2$C$\underline{H}_3$); 2.17 (3H,s,

1.20 (3H,d,J=7.0Hz, C$\underline{H}$$_3$-14); 0.91 (3H,d,J=6.0Hz, CH$_3$-17), δ$_C$(CDCl$_3$) 174.1, 166.8, 157.0, 117.5, 74.9, 71.2, 70.3, 68.9, 65.4, 63.5, 61.2, 55.6, 51.6, 42.8, 39.6, 33.9, 31.6, 28.4, 25.6, 24.6, 20.7, 19.1 and 12.7 m/e 454.2610 (0.6%; M$^+$ - H$_2$O; C$_{24}$H$_{38}$O$_8$ requires 454.2567), 227 (42%), 129 (50%), 111 (61%).

EXAMPLE 21

1R,S-Methoxycarbonyl-1R,S-cyclohexylmethyl monate

Sodium monate (0.80gm; 2.19mM) was dissolved in dry dimethylformamide (15ml) and hexamethylphosphoramide (15 drops). Methyl 2-bromo-2-cyclohexyl acetate (1.91gm; 8.13mM) was added and the reaction mixture stirred at room temperature for 64 hours. The solvent was then removed at reduced pressure and the residue partitioned between ethyl acetate and saturated sodium bicarbonate solution. The organic layer was washed with brine and dried over anhydrous magnesium sulphate. Removal of the solvent at reduced pressure gave a yellow oil, which was purified by column chromatography over silica gel(Type 60. 17gm).. Elution with 5% methanol/chloroform afforded the pure 1 R,S-methoxycarbonyl-1R,S-cyclohexylmethyl monate (by tlc and hplc) as a white foam (0.175gm; 16%). [α]$_D$$^{20}$ −6.2° (C,1%CHCl$_3$), λmax (EtOH) 224nm (εm 13,800),νmax (KBr) 3440, 1745, 1720, and 1645cm$^{-1}$. δ$_H$ (CDCl$_3$) 5.80 (1H,s, C$\underline{H}$=C); 4.79 (1H,d,J=4.0Hz, CO$_2$C$\underline{H}$); 3.69 (3H,s,CO$_2$CH$_3$); 2.18 (3H,s,

1.20 (3H,d,J=6.0Hz, CH$_3$-14); 0.90 (3H,d,J=7.0Hz, CH$_3$-17), δ$_c$ (CDCl$_3$) 170.8, 166.1, 158.8, 116.8, 76.1, 75.1, 71.4, 70.5, 69.1, and 68.8, 65.5, 61.3, 55.6, and 55.4, 51.9 and 51.8, 43.1, 42.9 and 42.8, 39.7, 29.1, 28.1, 26.0, 20.9, 19.6, and 19.33, 12.7 and 12.6, m/e 254.1526 (2.5%, C$_{14}$H$_{22}$O$_4$ requires 254.1518), 227.1284 (16%, C$_{12}$H$_{19}$O$_4$ requires 227.1283), 95 (85%), 90 (100%).

EXAMPLE 22 n-Octyl monate

Sodium monate (183mgs) was dissolved in DMF (5ml) and HMPA (1 drop) then sodium iodide (75mgs) and n-bromo-octane (0.2ml) were added. The solution was stirred for 1 day then evaporated to dryness, dissolved in ethyl acetate/water and organic layer washed with sodium bicarbonate solution and brine. After drying (MgSO$_4$) the solution was evaporated to an oil which was chromatographed on silica (10g) eluting with gradient of methanol/chloroform 0–5%. Fractions containing pure product (by tlc) were collected and evaporated to yield an oil (130mgs, 57%), [α]$_D$$^{20}$ − 10.2 (c,1.0CHCl$_3$), νmax (CHCl$_3$) 3400 (broad, OH's). 1703 (C=O), 1645 and 1150cm$^{-1}$, δ$_H$ (CDCl$_3$) 5.68 (1H,s,CH=C), 4.02 (2H,t,OC$\underline{H}$$_2$CH$_2$), 2.16 (3H,s,C$\underline{H}$$_3$CH=C), 0.90 (3H;d,C$\underline{H}$$_3$CH), δ$_C$ (CDCl$_3$) 166.9, 156.6, 117.7, 74.9, 71.4, 70.3, 69.0, 65.4, 64.0, 61.4, 55.6, 42.9 (two signals), 39.5, 31.8, 31.6, 29.2 (two signals), 28.8, 26.0, 22.6, 20.8, 19.1, 14.1, 12.7.

EXAMPLE 23 n-Butyl monate

Sodium monate (183mgs) was dissolved in DMF (5ml) and HMPA (1 drop) and treated with n-iodobutane (1ml) then stirred at room temperature overnight. The solution was evaporated to dryness dissolved in ethyl acetate/water and the organic layer washed with sodium bicarbonate and brine. After drying (MgSO$_4$) the solution was evaporated to an oil which was chromatographed on silica (10g) eluting with gradient of methanol/chloroform 0–5%. Fractions containing pure product (by tlc) were collected and evaporated to yield an oil (124mgs, 62%), [α]$_D$$^{20}$ −9.6° (c,1.0 CHCl$_3$), 3400 (broad, OH's), 1708 (C=O). 1650 and 1155cm$^{-1}$, δ$_H$ (CDCl$_3$) 5.69 (1H,s,C$\underline{H}$=C), 4.03 (2H,t,OC$\underline{H}$$_2$(CH$_2$)$_2$), 2.16 (3H,s,C$\underline{H}$$_3$C=C), 1.19 (3H,d,C$\underline{H}$$_3$-CH), 0.92 (5H,m,C$\underline{H}$$_3$CH and C$\underline{H}$$_3$(CH$_2$)$_3$), δ$_C$ (CDCl$_3$) 167.0, 156.7, 117.7, 74.4, 71.3, 70.3, 69.0, 65.4, 63.6, 61.3, 55.6, 42.9 (two signals), 39.5, 31.6, 30.8, 20.8, 19.2, 19.1, 13.7, 12.7.

EXAMPLE 24

Prop-2-enyl monate

Sodium monate (0.300gm; 0.82mM) was dissolved in dry dimethylformamide (10 ml) and stirred at room temperature for 3 days with allyl bromide (0.199gm; 1.64mM) and hexamethylphosphoramide (10 drops). The solvent was then removed at reduced pressure and the residue partitioned between ethyl acetate and saturated sodium bicarbonate solution. The organic layer was washed with brine and dried over anhydrous magnesium sulphate. Filtration and removal of the solvent at reduced pressure gave a yellow oil (0.349gm), which was purified by column chromatography over silica gel (Type 60; 14gm). Elution with 5% methanol/chloroform gave the pure prop-2-enyl monate as a colourless oil (220gm; 70%), [α]$_D$$^{20}$ − 11.4° (C, 1% CHCl$_3$), λ$_{max}$ (EtOH) 223nm (ε$_m$ 13,800), ν$_{max}$ (nujol) 3,400. 1710, 1645cm$^{-1}$. δ$_H$ (CDCl$_3$) 5.6–6.1 (2H, m, -C$\underline{H}$ = C protons); 5.05–5.5 CH$_3$ (2H, m, C = C$\underline{H}$$_2$); 4.54 (2H, d, J = 5.5Hz, CO$_2$C$\underline{H}$$_2$); 2.18 (3H, s, C=C); 1.19 (3H, d, J = 6.5Hz, C$\underline{H}$$_3$ - 14); 0.91 (3H, d, J = 7.0Hz, C$\underline{H}$$_3$ - 17). δ$_C$ (CDCl$_3$) 166.3, 157.6, 132.6, 118.0, 117.2, 74.9, 71.3, 70.3, 68.9, 65.4, 64.5, 61.3, 55.6, 42.8, 39.5, 31.6, 20.8, 19.2 and 12.7.

EXAMPLE 25

1-Carboxymethyl monate sodium salt

1-Methoxycarbonylmethyl monate (0.225gm; 0.54mM) was dissolved in methanol (22.5ml) and pH10 sodium hydroxide/sodium bicarbonate buffer solution (22.5ml) and stirred at room temperature for 18 hours. The pH was then adjusted to 9 and the methanol was removed at reduced pressure. The aqueous solution was washed with ethyl acetate in order to remove any starting material. The aqueous solution was relayered with ethyl acetate and the pH adjusted to 3.0 by the addition of 1N hydrochloric acid. The organic layer was dried over magnesium sulphate, filtered and the solvent removed to yield a colourless oil (0.170gm). This oil was dissolved in water by adjusting the pH to 7.0 by the addition of 0.1N sodium hydroxide solution. Freeze drying yielded the 1-carboxymethyl monate sodium salt as a white solid (0.150gm; 65%). [α]$_D$$^{20}$ − 18.8° (C, 1% CH$_3$OH),λ$_{max}$ 222nm (ε$_m$ 11,600). ν$_{max}$ (KBr) 3420, 1720 and 1620cm$^{-1}$. $\delta_H$(CDCl$_3$) 5.90 (1H, s, -C$\underline{H}$=C); 4.47 (2H, s, CO$_2$—C$\underline{H}_2$—CO$_2$); 2.15 (3H, s,

1.20 (3H, d, J = 6.0Hz, C$\underline{H}_3$-14); 0.93 (3H, d, J = 7.0Hz, C$\underline{H}_3$-17), $\delta_C$(CDCl$_3$) 175.1, 167.4, 158.9, 116.4, 74.2, 69.4 (split), 68.3, 64.8, 62.5, 61.2, 56.5, 41.7, 38.7, 30.8, 18.7, 18.0, 10.9.

EXAMPLE 26

1-Carbamoylmethyl monate

Sodium monate (183 mgs) in DMF (5ml) and HMPA (1 drop) was treated with 2-chloroacetamide (95mgs) and sodium iodide (150 mgs). After stirring overnight solution evaporated to dryness dissolved in ethyl acetate/water and washed with sodium bicarbonate and brine solutions. The aqueous fractions were found to contain product (tlc) and were freeze dried then extracted with methanol. The combined methanol and ethyl acetate solutions were evaporated to dryness and residue chromatographed on silica (8 g) eluting with gradient of methanol/chloroform 0–4%. Fractions containing pure product (by tlc) were combined and evaporated to yield crystalline product (77 mgs, 36%), $\nu_{max}$ (CHCl$_3$) 3400 (broad, OH's), 1712 (C=O's) and 1650cm$^{-1}$, $\delta_H$(CDCl$_3$) 5.72 (1H, s, C$\underline{H}$=C), 3.64 (2H, s, CH$_2$CONH$_2$), 2.18 (3H, s, C$\underline{H}_3$C=C), 1.20 (3H, d, C$\underline{H}_3$CH), 0.91 (3H, d, C$\underline{H}_3$CH).

EXAMPLE 27

3-Methoxycarbonylprop-2en-1-yl monate

Sodium monate (106mgs) was dissolved in DMF (5ml) treated with methyl 4-bromocrotonate (0.2 ml) then stirred overnight at room temperature. The solution was evaporated to dryness, dissolved in ethyl acetate/water and the organic layer washed with aqueous sodium bicarbonate and brine. After drying (MgSO$_4$) the solution was evaporated to dryness and the oil chromatographed on silica (4 g) eluting with gradient of methanol/chloroform 0–5%. Fractions containing pure product (by tlc) were collected and evaporated to an oil (17mgs, 14%) $\nu_{max}$ (CHCl$_3$) 3400 (broad, OH's), 1718 (C=O's), 1670 and 1648cm$^{-1}$, $\delta_H$ (CDCl$_3$) 6.92 (1H, 2 X m, j=16, CH$_2$C$\underline{H}^t$=C$\underline{H}$-), 5.98 (1H, 2×m, J=16, CH$_2$CH$^t$=C$\underline{H}$), 5.77 (1H, s, C$\underline{H}$=C), 4.72 (2H, m, C$\underline{H}_2$CH$^t$=CH) 3.70 (3H, s, CO$_2$C$\underline{H}_3$), 2.19 (3H, s, C$\underline{H}_3$C=C), 1.20 (3H, d, C$\underline{H}_3$CH), 0.91 (3H, d, C$\underline{H}_3$CH).

EXAMPLE 28

2,3-Epoxypropyl monate.

Sodium monate (0.267gm; 0.73mM) was dissolved in dry dimethylformamide (10ml). Epibromohydrin (0.20gm; 1.46mM) and hexamethylphosphoramide (10 drops) were added and the solution stirred at room temperature for 3 days. The solvent was then removed at reduced pressure and the residue partitioned between ethyl acetate and saturated sodium bicarbonate solution. The organic layer was washed with brine and dried over anhydrous magnesium sulphate. Filtration and removal of the solvent at reduced pressure gave a yellow oil (0.450gm) which was purified by column chromatography over silica gel (Type 60; 11gm). Elution with 5% methanol/chloroform gave the pure (by hplc and tlc) 2,3-epoxypropyl monate as a colourless oil (0.240gm; 83%), $\nu$max (CH Br$_3$) 3450, 1715, 1645, 1222 and 910cm$^{-1}$, $\delta_H$ (CDCl$_3$) 5.76 (1H, s, C$\underline{H}$=C); 4.15 (2H,2 × AB, CO$_2$C$\underline{H}_2$); 2.20 (3H, s,

1.22 (3H, d, J=6.0Hz, C$\underline{H}_3$-14); 0.92 (3H, d, J=7.0Hz, (C$\underline{H}_3$-17). $\delta_{C\,(CDCl_3)}$ 166.2, 158.4, 116.8, 75.0, 71.2, 70.4, 69.0, 65.5, 64.2, 61.2, 55.6, 49.6, 44.8, 42.9, 39.6, 31.7, 20.8, 19.3, 12.6.

EXAMPLE 29

2-Propynyl monate

Sodium monate (0.267gm; 0.73mM) was dissolved in dry dimethylformamide (10ml). Propargyl bromide (0.174gm; 1.46mM) and hexamethylphosphoramide (10 drops) were added and the solution stirred at room temperature for 16 hours. The solvent was then removed at reduced pressure and the residue partitioned between ethyl acetate and saturated sodium bicarbonate solution. The organic layer was washed with brine and dried over anhydrous magnesium sulphate. Filtration and removal of the solvent at reduced pressure gave a yellow oil (0.390gm), which was purified by column chromatography over silica gel (Type 60; 11 gm). Elution with 5% methanol/chloroform gave the pure (hplc and tlc) 2-propynyl monate as a colourless oil (0.225gm; 81%) $\nu$max (CHBr$_3$) 3420, 2110, 1718 and 1645cm$^{-1}$. $\delta_H$(CDCl$_3$) 5.75 (1H, s, C$\underline{H}$=C); 4.66 (2H, d, J=3.0Hz, CO$_2$C$\underline{H}_2$); 2.20 (3H, s,

1.20 (3H, d, J=6.5Hz, CH$_3$-14); 0.92 (3H, d, J=6.5Hz, CH$_3$-17), $\delta_C$(CDCl$_3$) 165.6, 158.9, 116.5, 78.3, 75.0, 74.6, 71.2, 70.4, 69.0, 65.5, 61.3, 55.6, 51 2, 42.9, 39.6, 31.7, 20.8, 19.4, 12.7.

BIOLOGICAL DATA (a) Tables 1 and 2 show the M.I.C Values ($\mu$g/ml) for several compounds of this invention against 6 Gram-positive organisms and against *N. gonorrhoae* and *H. influenzae*.

(b) Table 3 gives the, in vitro antimycoplasmal activities of certain esters of monic acid in terms of their M.I.C. values.

TABLE 1

| Organism | COMPOUND OF EXAMPLE NUMBER | | | | | | | | |
|---|---|---|---|---|---|---|---|---|---|
| | 10 | 9 | 6 | 11 | 13 | 12 | 14 | 15 | 16 |
| Bacillus subtilis | 0.2 | 0.5 | 0.1 | 1.0 | 0.2 | 5.0 | 12.5 | 5.0 | 1.0 |
| Staph. aureus Oxford | 0.2 | 0.5 | 0.2 | 1.0 | 1.0 | 2.5 | 5.0 | 5.0 | 1.0 |
| Staph. aureus Russell | 0.2 | 0.5 | 0.2 | 2.5 | 1.0 | 5.0 | 12.5 | 12.5 | 2.5 |
| Staph. aureus 1517 | 0.2 | 1.0 | 0.2 | 2.5 | 2.5 | 5.0 | 12.5 | 12.5 | 2.5 |
| Strep. faecalis I | >100 | >100 | >100 | >100 | >100 | >100 | >100 | >100 | >100 |

TABLE 1-continued

| | COMPOUND OF EXAMPLE NUMBER | | | | | | | | |
|---|---|---|---|---|---|---|---|---|---|
| Organism | 10 | 9 | 6 | 11 | 13 | 12 | 14 | 15 | 16 |
| Strap. pyogenes CN10 | 0.2 | 2.5 | — | 2.5 | 1.0 | 0.2 | 25 | 25 | 2.5 |
| N. gonorrhoae | 0.02 | 0.1 | NT | 0.2 | 0.2 | 0.1 | NT | NT | 1.0 |
| H. influenzae | 0.1 | 0.5 | 0.2 | 0.2 | 1.0 | 0.2 | 2.5 | 12.5 | 0.5 |

NT = Not tested

TABLE 2

| | COMPOUND OF EXAMPLE NUMBER | | | | | | | |
|---|---|---|---|---|---|---|---|---|
| Organism | 17 | 18 | 19 | 20 | 21 | 22 | 23 | 24 |
| B. subtilis | 5.0 | 2.5 | 1.0 | 0.1 | 5.0 | 0.5 | 0.1 | 0.2 |
| S. aureus Oxford | 5.0 | 5.0 | 1.0 | 0.2 | 10 | 0.5 | 0.2 | 0.2 |
| S. aureus Russell | 10 | 25 | 2.5 | 0.5 | 25 | 2.5 | 0.5 | 0.5 |
| S. aureus 1517 | 25 | 25 | 5.0 | 0.5 | 50 | 2.5 | 1.0 | 1.0 |
| Strep. faecalis I | >100 | >100 | >100 | >100 | >100 | >100 | 50 | 50 |
| Strep. pyogenes GpA | 50 | 25 | 25 | 0.5 | 25 | 2.5 | 1.0 | 2.5 |
| N. gonorrhoae | NT | NT | NT | 0.1 | NT | NT | 0.5 | NT |
| H. influenzae | 2.5 | 5.0 | 1.0 | 0.1 | 25 | 2.5 | 0.1 | 0.1 |

NT = Not tested

TABLE 3.

The antimycoplasmal activities of esters of monic acid
M.I.C. (μg/ml)

| Compound | Example No | M.gallisepticum 56 | M.suipeumoniae (Laber) | M.dispar H225 | M.pneumoniae 429A |
|---|---|---|---|---|---|
| Methyl monate | 9 | 1.5 | <0.5 | <0.5 | 0.6 |
| Benzyl monate | 6 | <0.5 | <0.5 | <0.5 | 250 |
| Methoxycarbonyl-methyl monate | 11 | >250 | >250 | 250 | >250 |
| 4-Methoxycarbonyl butyl monate | 12 | 250 | 15.6 | 1.0 | 125 |
| 10-Methoxycarbonyl-decyl monate | 13 | 15.6 | 31.25 | 1.0 | 15.6 |

Improved Isolation of Monic Acid

Pure Crystalline pseudomonic acid (1.00gm; 2mM) was dissolved in trimethylorthoformate (10ml) and stirred at R.T. for 30 minutes with p-toluene sulphonic acid (10mg). The solvent was then removed at reduced pressure and the residual oil immediately dissolved in 1N NaOH (10ml; 10mM). The solution was stirred at 65° C for 3 hours, then cooled and the pH adjusted to 7.0 with conc. HCl. Methanol (10ml) was added, the pH was adjusted to 2.0 with 5N HCl and the solution was stirred at R.T. for 15 minutes. The pH was then raised to an maintained at 9.0 – 9.5 with NaOH for 3 hours, when HPLC indicated complete hydrolysis of the O-formate. The pH was adjusted to 7.0 and the solution evaporated to dryness at reduced pressure. The residual solid was dissolved in water (20ml), saturated with NaCl, layered with ethyl acetate and acidified to pH 3. The organic layer was separated and the aqueous layer further extracted with 5 × 50ml ethyl acetate. The combined organic extracts were dried over anhydrous $MgSO_4$ and the solvent removed at reduced pressure to yield a yellow oil (1.377gm; 1433/50/1.) Trituration with dry diethyl ether gave the monic acid (>90% pure by HPLC and TLC) as a white solid (0.393gm; 1433/50/2). A further 0.146gm (1433/50/3) white solid was obtained from the mother liquors. Total yield = 0.539gm (78%). M. pt. 130° – 133° C. The product was identical to authentic monic acid by HPLC and TLC (chloroform/acetate/acetic acid 50:50:7).

What we claim is:

1. A compound of formula (II):

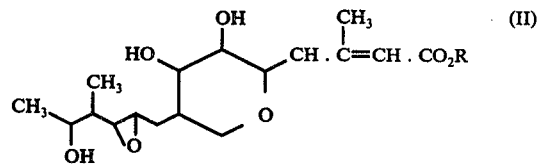

wherein R is $C_{1-20}$ alkyl, $C_{2-8}$ alkenyl or $C_{2-8}$ alkynyl.

2. A compound as claimed in claim 1 wherein R is a $C_{1-10}$ alkyl group.

3. A compound as claimed in claim 1 wherein R is methyl or ethyl.

4. A compound as claimed in claim 1 wherein the double bond in formula (II) is in the E configuration.

5. A compound as claimed in claim 1 wherein R is ethyl.

6. A compound as claimed in claim 1 wherein R is methyl.

* * * * *